(12) United States Patent
Tsolkas et al.

(10) Patent No.: US 6,413,515 B1
(45) Date of Patent: Jul. 2, 2002

(54) AVIAN, VITELLINE ANTIBODIES DIRECTED AGAINST HIV ANTIGENS

(75) Inventors: Panagiotis Tsolkas, Luneburg; Hartmut Kobilke, Damsdorf, both of (DE)

(73) Assignee: Ovogenix Immunpharma GmbH, Berlin (DE)

( * ) Notice: Subject to any disclaimer, the term of this patent is extended or adjusted under 35 U.S.C. 154(b) by 0 days.

(21) Appl. No.: 08/952,339

(22) PCT Filed: Mar. 12, 1996

(86) PCT No.: PCT/EP96/00497

§ 371 (c)(1),
(2), (4) Date: Jul. 13, 1998

(87) PCT Pub. No.: WO97/33915

PCT Pub. Date: Sep. 18, 1997

(Under 37 CFR 1.47)

(51) Int. Cl.⁷ ............................................. A61K 39/395
(52) U.S. Cl. ............................... 424/157.1; 424/130.1; 424/159.1; 424/160.1; 530/389.4
(58) Field of Search .......................... 435/5; 424/130.1, 424/157.1, 159.1, 160.1; 530/389.4

(56) References Cited

U.S. PATENT DOCUMENTS

| | | | |
|---|---|---|---|
| 4,357,272 A | 11/1982 | Polson | 424/8 |
| 4,550,019 A | 10/1985 | Polson | 424/85 |
| 4,748,012 A | 5/1988 | Stolle et al. | 424/87 |
| 5,080,895 A | 1/1992 | Tokoro | 424/85.8 |

FOREIGN PATENT DOCUMENTS

| | | |
|---|---|---|
| EP | 225254 | 11/1986 |
| GB | 057451 A | 4/1981 |
| WO | 0152270 A3 | 1/1988 |
| WO | WO8901339 | 2/1989 |
| WO | WO9009805 | 9/1990 |

OTHER PUBLICATIONS

R. Schade et al., Chicken Yolk Antibodies, Production and Application, IgY–Technology, Springer–Verlag Berlin Heidelberg, New York (2001) pp. 201, 203, 204.

H. Hatta et al., Prevention of Fish Disease Using Egg Yolk Antibody, CAB International, Wallingford, UK (1994) Chapter 20, 1ˢᵗ page only.

Wiedemann et al., J. Vet. Med. B, vol. 38 (1991) pp. 283 1st page only.

O'Farrelly et al., Infection and Immunity, (1992) pp. 2593, 1st page only.

Erhard et al., J. Vet. Med. A, vol. 43 (1996) pp. 217, 1st page only.

Yokoyama et al., Infection and Immunity, vol. 60, No. 3 (1992) pp. 998.

Ikemori et al., Veterinary Microbiology, vol. 58 (1997) pp. 105.

Jackson et al, Passive Immunoneutralisation of Human Immunodeficiency Virus in Patients with Advanced Aids; The Lancet Sep. 17, 1988; p647 incomplete.

Yolken et al.; Antibodies to Rotaviruses in Chicens' Eggs: A Potential Source of Antiviral Immunoglobulins Suitable for Human Consumption; Pediatrics vol. 81, No. Feb. 1988; pp. 291–295.

Bartz et al., Prevention of Murine Rotavirus Infection with Chicken Egg Yolk Immunoglobulins; The Journal of Infectious Diseases, vol. 142; No. 3, Sep. 1980; pp 439–441.

Karpas et al., Polymerase Chain Reaction Evidence for Human Immunodeficiency Virus 1 Neutralization by Passive Immunization in Patients with AIDS and AIDS–Related Complex; 1990; Proc. Natl. Acad. Sci. USA, vol. 87, pp 7613–7617.

Larsson et al., Chicken IgV: Utilizing the Evolutionary Difference; Comp. Immun. Microbiol. infec. Dis. vol. 13, No. 4 1990; pp 199–201.

Kuroki et al., Passive Protection Against Bovine Rotavirus–Induced Diarrhea in Murine Model by Specific Immunoglobulins from Chicken Egg Yolk; Veterinary Microbiology 37; 1993; pp 135–146.

Kageyama et al.; Human Antibody to Matrix Protein; Aidsline—1980 12/94—Meeting Abstract.

Lange et al.; Decline of Antibody Reactivity to Outer Viral Core Protein; Aidsline—1980 12/94 absract only.

Karpas et al.; Passive Immunization in HIV Disease; Aidsline 1980 12/94 Clincal Trial, Meeting Abstract.

Hague et al.; Infusion of Anti P24 Antibody Rich Plasma in Two Children with Persistent HIV Antigenaemia—Abstract—1989.

Lefrere et al.; Passive Immunotherapy in AIDS: State of Phase II Trial; Aidsline—1980–Jun. 1994 Clinical Trial abstract only.

Lefrere et al.; Passive Immunotherapy in AIDS: Transfusion of Plasma Rich in Anti–p25 Antibody Phase I Trail—Abstract May 1991.

Lefrere et al.; Passive Immunotherapy in AIDS: results of a double blind randomised study; —Abstract 1994.

Bainbridge et al.; Passive Immunotherapy (PIT) in HIV disease: study of patients and donors; Aidsline—1980—12/94—Meeting Abstract.

Nishino et al.; Major Core Proteins, p24s, of human, simian, and feline immunodeficiency viruses are partly expressed on the surface of the virus–infected cells; Aidsline 1980, Jun. 1994—abstract only 1992 Vaccine 10(10)677–83.

(List continued on next page.)

*Primary Examiner*—Jeffrey Stucker
(74) *Attorney, Agent, or Firm*—Birch, Stewart, Kolasch & Birch, LLP.

(57) ABSTRACT

The present invention is drawn to avian vitellin antibodies that are immunologically reactive with HIV antigens, a process for the preparation thereof, a use thereof and a food substance in the form of a hen's egg containing the antibodies. The antibodies of the present invention are produced by immunizing hens with HIV antigens, in particular HIV core antigens and concentrating the antibodies in the egg yolk. The antibodies are suitable for passive immunization of mammals.

11 Claims, No Drawings

OTHER PUBLICATIONS

Gregersen et al.; Antibody—and complement–mediated lysis of HIV–infected cells and inhibition of viral replication; Aidsline—1980; Jun. 1994—Journal Article abstract only J. Med. Virol 1990 Apr. 30(4) 287–93.

Franke et al.; Inhibition of HIV–1 infection in vitro by murine monoclonal anti–p24 antibodies; Aidsline—19890, Jun. 1994—abstract only.

Yokoyama et al., Passive Protective Effect of Chicken Egg Yolk Immunoglobulins Against Experimental Enterotoxigenic *Escherichia Coli* Infection in Neonatal Piglets; Veterinary Bulletin vol. 62 No. 6; 1992, Abstract.

Wiedemann et al., Chicken Egg Antibodies for Prophylaxis and Therapy of Infectious Intestinal Diseases III; In vivo Tenacity Test in Piglets with with Artificial Jejunal Fistula; 1990; Abstract.

AVIAN, VITELLINE ANTIBODIES DIRECTED AGAINST HIV ANTIGENS

The invention relates to avian, vitelline antibodies directed against HIV antigens, methods for their preparation, and their use. These antibodies—monospecific, polyclonal egg yolk antibodies from SPF chickens (specified pathogen-free chicken)—are suitable in HIV (human immunodeficiency viruses) diagnostics and in the therapeutical use on HIV-positive patients in the symptom-free stage, and where symptoms of ARC (AIDS-related complex) or AIDS (acquired immunodeficiency syndrome) are present.

Since the end of the last century it is well-known that considerable amounts of antibodies (Ab) may be accumulated in chicken egg yolk (Klemperer F., Arch. exptl. Pathol. Pharmakol. 31 (1893) 356–382). Over the last ten years, there were massively increasing efforts to recover antibodies from bird eggs and utilize them for medical purposes. In contrast to other methods, the antibody accumulation and recovery via bird's egg is a bloodless method, since blood withdrawal is not required for Ab recovery (Schade, R. and A Hlinak: Mh. Vet.-Med. 48 (1993) 91–98, Gustav Fischer Verlag, Jena).

The well-known methods comprise immunization of chickens with an antigen and recovery of the antibodies (IgY, yolk antibodies) from the eggs/egg yolk (US=US patent, GB=British patent, DD=East German application, DE=German unexamined application (OS)/patent specification (PS), EP=European patent, WO=PCT(Patent Cooperation Treaty) application: Immunologically reactive preparations (Egg Yolk Antibodies, Polson, A.: DE 29 51 412), Egg Yolk Antibodies (Polson, A.: GB 2,057,451, U.S. Pat. No. 4,357,272), Fowl Egg Antibodies (Polson, A.: U.S. Pat. No. 4,550,019), Specific Chicken Egg Antibodies (Tsuda, K. et al.: EP 503,293), Specific antibody-containing substance from eggs (Tokoro, H.: U.S. Pat. No. 5,080,895, EP 225, 254).

Passive immunization of mammals using antibodies recovered from a fowl species has also been described (Stolle, R. and L. R. Beck: DE 35 04 221, U.S. Pat. No. 4,748,018, EP 152,270). Therein, immunizing quantities of an antibody recovered from eggs of a fowl species immunized with the antigen causing the mammal's disease are administered to the mammal.

Another well-known example is the successful passive immunization against rotavirus infections in mammals using avian, vitelline antibodies (Bartz, C. R. et al., The Journal of Infectious Diseases, Vol. 142, No. 3, 1980, 439–441; Yolken, R. H. et al., Pediatrics (1988) 81 (2) 291–295; Kuroki, M. et al., Veterinary Microbiology, 37 (1993) 135–146); and the passive immunization of mammals using avian antibodies against *E. coli* (Wiedemann, V. et al., Journal of Veterinary Medicine, Series B (1990) 37 (3), 163–172; ibid., (1991) 38(4), 283–291; Yokoyama, H. et al., Infection and Immunity (1992) 60 (3), 998–1007).

The structural differences between avian and mammal IgG are explained on the basis of the phylogenetic divergence of birds and mammals. Above all, they are apparent from the differences in molecular weights and sedimentation constants: chicken IgG 170,000 or 174,000, human IgG 150,000 daltons (Larsson, A. and J. Sjöquist, Comp. Immun. Microbiol. infect. Dis., Vol. 13, No. 4, pp 199–201, 1990; Jürgens, L.: Reinigung von IgG und IgG-Antikörpern aus dem Eidotter, Ph.D. Thesis 1987, Ludwig-Maximilians-Universität, Munich).

It is also well-known that HIV-infected cells express core antigens on their cell membranes, e.g. p24 antigen (Nishino, Y. et al., Vaccine, 1992, 10 (10) 677–683). An in vitro inhibition of HIV infection using anti-p24 antibodies is described by Gregersen J. P. et al. (J. Med. Virol. 1990, 30(4) (287–293) and Franke, L. et al. (J. Med. Virol. 1992, 37 (2) 137–142). The influence of a high anti-HIV p24 antibody titer on the condition of HIV-positive patients is the subject matter of WO 89/01339 (Cummins, L. M. et al.), and that with the proteins gp41 and p24 of corresponding antibodies is the subject matter of WO 90/09805 (Zolla-Pazner, S. et al.). The assessment of the immunologic defense pattern of a patient is the essence of DD 299 090, according to which the anti-HIV Ab content of the patient after treatment with monoclonal antibodies (mAb) particularly directed against the HIV protein p24 (anti-HIV p24 mAb) is determined using ELISA (Enzyme-Linked Immunosorbent Assay).

The symptoms of ARC and AIDS, respectively, begin with a massive decrease or total disappearance of the anti-p24 antibodies from the serum of HIV-positive patients (Jackson, G. G., The Lancet, Sep. 17, 1988, 647–651; Karpas, A. et al., Proc. Natl. Acad. Sci. USA, Vol. 87, pp 7613–7617, October 1990), whereas patients having a high anti-p24 antibody titer remain symptom-free. Several authors conducted a passive immunization with patients in the ARC and AIDS stages (Karpas, A. et al. 1990, ibid.; Karpas, A. et al., Int. Conf. AIDS, Jun. 6–11, 1993 9 (1), 244, Abstract No. PO-A28-0659; Jackson, G. G., ibid.; Hague, R. et al., Int. Conf. AIDS, Jun. 4–9, 1989 , 5, 328, Abstract No. T.B.P. 246; Lefrere, J. J. et al., a) Int. Conf. AIDS, Jun. 6–11, 1993 9 (1), 246, Abstract No. PO-A28-0667; b) Rev. Fr. Transfus. Hemobiol., May, 34 1994 (3), 199–211; c) Int. Conf. AIDS, Aug. 7–12, 1994 10 (1), 226, Abstract No. PBO335), where plasma from symptom-free patients (up to 500 ml) with high anti-p24 antibody titer was transfused to patients in the ARC and AIDS stages after the viruses in the plasma had been inactivated by heat. Two hours after transfusion, p24 could not be detected in the serum anymore; also, the number of HIV-infected cells was reduced. Patients in the ARC stage showed significant amelioration of the clinical symptoms up to complete absence of symptoms. There was no decrease in the number of T4-helper cells anymore.

To date, survival with absence of symptoms for periods as long as 22 and 35 months has been described. With patients in an advanced stage of AIDS, remission continued for 6 to 22 months, depending on the state of the individual severity level of the disease at the time treatment had begun, with present aviremia and sufficient antibody level. In the ARC stage, the clinical remission continued 22 months beyond the KARPAS study, with present aviremia and stable CD4+ T-cell number (Karpas, A. et al., Int. Conf. AIDS, Jun. 6–11, 1993, 9 (1), 244, Abstract No. PO-A28-0659; Bainbridge, D. et al., Int. Conf. AIDS, Aug. 7–12, 1994, 10 (1), 216, Abstract No. PB 0293).

The invention is based on the object of providing antibodies directed against HIV antigens, which may be administered to HIV-infected patients. The object was accomplished by immunizing chickens with HIV antigens, thereby accumulating anti-HIV antibodies in the egg yolk. Surprisingly, it was found that administering these antibodies in the form of an oral administration of dried egg yolk or as antibody extract after isolation from egg yolk and work-up results in increased antibody serum titer values, and that avian antibodies in mammals are capable of binding the mammal complement.

As a result of the phylogenetic divergence between birds and mammals, fowl species for the production of antibodies against mammal diseases had been excluded, particularly for the reason that chicken protein was foreign to the human immune system and would give rise to allergic reactions when used repeatedly (DE 35 04 221 C2 dated May 19, 1994). According to Gippner-Steppert et al., chicken antibodies —in contrast to mammal antibodies—would give no reaction with mammal complement factor C1 and mammal Fc-receptors (Gippner-Steppert, C. and M. Jochum: "Production and purification of chicken polyclonal anti-peptide antibodies specific for fibrino-elastase-peptide A-alphal-21", lecture held during the public annual colloquium of the Surgical-Medical Clinic of the LMU Munich, Feb. 4, 1994).

The antibodies of the invention are novel both as avian antibodies and in their structure. They differ from well-known antibodies in molecular weight, sedimentation constant and isoelectric point.

According to the invention, particularly those antibodies are used which are directed against HIV core antigens. The most important role is assigned to the antibody derived from the core antigen p24, followed by the HIV proteins p17, p7 (9), p12, p66, and p32 (Kageyama, S. et al., Int. Conf. AIDS, Aug. 7–12, 1994, 10 (2), 86, Abstract No. PA 0224).

According to present knowledge, it appears that the anti-p24 antibodies of HIV-positive patients (HIV-1 and HIV-2) protect most effectively from the ARC and AIDS stages to occur. It is not clear as yet, to what extent other antibodies have an additional effect against core antigens.

The antibody titer against core protein p17 decreases earlier than the anti-p24 antibody (Lange, J. M. et al., AIDS, Sep. 1 1987, (3), 155–59).

The anti-core antibodies of the invention, and particularly the antibody against p24 antigen, result in absence of symptoms to a large extent and prolongation of life in ARC stage patients.

For mere logistic reasons, however, only a small circle of affected persons may benefit from the plasma transfusion method of treatment described above.

The avian, vitelline antibodies against core proteins according to the invention offer the advantage that they are produced in large amounts by chickens and transferred to the egg yolk. According to the invention, the antibodies are administered parenterally in a highly purified form, but also on the oral route as dry egg yolk or antibody extract, because they are thermally stable and acid-resistant to a high extent. With the solution of the invention, a new kind of food is offered: the chicken's egg containing anti-HIV antibodies, wherein the antibodies are accumulated in the egg yolk in particular, but not exclusively.

In particular, core antigens, preferably p24 and p17 are suitable as HIV antigens. Using SPF chickens, they result in the corresponding SPF chicken polyclonal antibodies according to the invention.

The method of the invention for producing avian, vitelline antibodies directed against HIV antigens comprises immunization of chickens with HIV antibodies, particularly core antigens, preferably the core proteins p24 and/or p17, thereby accumulating the antibodies in the egg and egg yolk, respectively, and optional isolation therefrom.

The antibodies of the invention may be used in the passive immunization of mammals. They are suited to be administered to HIV-positive patients in order to produce high antibody serum titers.

The isolation of the IgY antibodies of the invention is effected from aqueous yolk solutions according to well-known procedures, using PBS (phosphate-buffered sodium chloride solution) as solvent and subsequent centrifugation, precipitation of immunoglobulins by means of precipitating agents such as polyethylene glycol (PEG), sodium, dextran or ammonium sulfate and/or chromatographic purification such as gel filtration or ion exchange (Schade, R. and A. Hlinak: Mh. Vet.-Med. 48, 1993, p. 95, Gustav Fischer Verlag, Jena).

With reference to the embodiments, the invention will be illustrated in more detail.

Embodiments

EXAMPLE 1

General procedure

The immunization of chickens, especially SPF chickens, is effected using synthetic, non-infectious HIV core complete antigens and a) Freund's complete adjuvant (FCA)

b) Freund's incomplete adjuvant (ICFA)

The sampling of blood and egg yolk was effected using pools each comprising 5 chickens of the antigen test group and a negative control group. The injection dose was 1.0 ml i.m. into the pectoral muscles into 4 depots each having 0.5 ml of resuspended synthetic antigen and adjuvant.

Start: Young chickens from the 15th week of life on.

End: 70th week of life (end of laying).

1.1. Initial immunization (base immunization) using 200 μg of synthetic HIV core complete antigen (protein) and FCA and blood zero sample on day "0" ($I_0$ sample).

1.2. 1st boosting (2nd immunization) on day 28 with blood and egg yolk sample $I_1$ for serological antibody control (IgG/IgY), including negative control group. All boostings were carried out using ICFA.

1.3. 2nd boosting (3rd immunization) on day 56 with $I_2$ blood and egg yolk samples including negative control group.

1.4. 3rd boosting (4th immunization) on day 84 with $I_3$ blood and egg yolk samples including negative control group.

1.5. $I_4$ blood and egg yolk samples on day 98, including negative control group.

1.6. $I_5$ blood and egg yolk samples on day 112, including negative control group.

1.7. $I_6$ blood and egg yolk samples on day 140, including negative control groups.

1.8. $I_7$ blood and egg yolk samples on day 168, including negative control groups.

1.9. 4th boosting (5th immunization) on day 220 with $I_8$ blood and egg yolk samples including negative control groups.

1.10. Egg yolk isolation and yolk separation are effected according to a batch process including final purification and extraction of the specific HIV antibodies against core complete antigens (proteins) (Schade R. and A. Hlinak, Mh. Vet.-Med. 48, 1993, p. 95, Gustav Fischer Verlag, Jena: IgY- Präparation, Extraktion vitelliner Antikörper).

1.11. IgY determination

The qualitative and quantitative determinations of the specific polyclonal IgY egg yolk antibodies amounting to 175 mg of antibodies/egg yolk are effected according to Schade R. and A Hilinak (1993), ibid.

The quantitative determination is effected via specific antibody titer examinations on yolk homogenizate using indirect ELISA, and that of the specific antibody content/ quantity unit of yolk is effected via affinity chromatography (using purified and separated antibody extract after vacuum dialysis).

EXAMPLE 2

Use of HIV p24 Antigen

As in Example 1, using HIV core p24 antigen.

EXAMPLE 3

Use of HIV p17 Antigen

As in Example 1, using HIV core p17 antigen.

EXAMPLE 4

Isolation of Pure Antibodies

This is effected according to a batch process (Schade R. 1993, cf., Example 1.10), for parenteral and oral therapy.

What is claimed is:

1. Avian, vitelline antibodies which are immunologically reactive with HIV antigens.

2. The antibodies according to claim 1, wherein said antibodies are immunologically reactive with HIV core proteins.

3. The antibodies according to claim 1 or 2 are immunologically reactive with HIV core proteins p24 and p17.

4. Avian, vitelline polyclonal antibodies directed against HIV antigens, wherein said antibodies are produced by immunizing chickens with HIV antigens and preparing the egg yolk from eggs laid by the chickens.

5. The antibodies according to claim 4, wherein said HIV antigens are HIV core proteins, and SPF (specified pathogen-free) chickens are immunized with said HIV core proteins.

6. The antibodies according to claim 5, wherein said core proteins are core proteins p24 and/or p17.

7. A method of passive immunization comprising administering the antibodies according to claim 1 or 4, to a mammal.

8. A method for producing avian, vitelline antibodies immunologically reactive with HIV antigens, which comprises immunizing chickens with HIV antigens, and accumulating the antibodies in the egg yolk.

9. The method according to claim 8, wherein HIV core antigens, are used as antigens.

10. A method for producing high antibody serum titers against HIV antigens which comprises parenterally administering to an HIV-positive patient in need thereof avian, vitelline antibodies directed against HIV antigens.

11. The method of claim 9, wherein said HIV core antigens are core proteins p24 and/or p17.

* * * * *